United States Patent [19]

Bender et al.

[11] 4,175,127

[45] Nov. 20, 1979

[54] PYRIDYL SUBSTITUTED 2,3-DIHYDROIMIDAZO[2,1-b]THIAZOLES

[75] Inventors: Paul E. Bender, Cherry Hill; Ivan Lantos, Blackwood, both of N.J.

[73] Assignee: SmithKline Corporation, Philadelphia, Pa.

[21] Appl. No.: 946,260

[22] Filed: Sep. 27, 1978

[51] Int. Cl.$^2$ .................... C07D 513/04; A61K 31/44
[52] U.S. Cl. .................................... 424/263; 546/271; 546/277
[58] Field of Search .......................... 546/271; 424/263

[56] References Cited

U.S. PATENT DOCUMENTS 4,064,260  12/1977  Cherkofsky .......................... 260/301

FOREIGN PATENT DOCUMENTS 1488271  7/1967  France ..................................... 546/135
1488322  7/1967  France ..................................... 546/271

*Primary Examiner*—Alan L. Rotman
*Attorney, Agent, or Firm*—William H. Edgerton

[57] ABSTRACT

The compounds are 5/6-pyridyl-phenyl-2,3-dihydroimidazo[2,1-b]thiazoles which have utility as intermediates and/or as having antiarthritic activity. A preferred group of compounds is 5-(4-pyridyl)-6-(4-substituted phenyl)-2,3-dihydroimidazo[2,1-b]thiazoles which have significant anti-arthritic activity.

13 Claims, No Drawings

PYRIDYL SUBSTITUTED 2,3-DIHYDROIMIDAZO[2,1-b]THIAZOLES

This invention relates to new 2,3-dihydroimidazo[2,1-b]thiazoles having, in the 5 and 6 positions, pyridyl or phenyl groups at least one of which is pyridyl. These compounds have utility as pharmacodynamic agents or as intermediates.

DESCRIPTION OF THE ART

Certain 2,3-dihydroimidazo[2,1-b]thiazoles having substituted phenyl substituents at the 5,6-position are described to the antiinflammatory, analgesic or antipyretic agents, U.S. Pat. No. 4,064,260, Belgian Pat. Nos. 858,978 and 852,259.

Pyridyl substituents have been inserted on heterocyclic ring systems but to our knowledge never on 2,3-dihydroimidazo[2,1-b]thiazole, see German Pat. No. 2,221,546, British Pat. No. 1,464,259, and French Pat. Nos. 2,271,213 and 1,488,322. See U.S. Pat. No. 3,707,475 which discloses certain heterocyclic substituted imidazoles lacking a 2-thio substituent.

DESCRIPTION OF THE INVENTION

The compounds of this invention are represented by the following formula:

FORMULA A

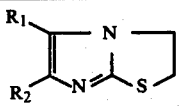

in which:

$R_1$ and $R_2$, being the same or different, but one of which always being pyridyl, are pyridyl or phenyl optionally substituted by one lower alkoxy, lower alkyl, lower alkylthio, chloro, fluoro, bromo or trifluoromethyl; or a pharmaceutically acceptable acid addition salt or oxide derivative thereof.

The pyridyl substituents may be attached at the 2, 3 or 4 position of the pyridyl ring with 4-position being preferred. Said lower alkyl or lower alkoxy groups are straight or branched chains of from 1–5 carbon atoms preferably of 1 or 2 carbon atoms.

Particular compounds of this invention are represented by Formula A in which $R_1$ is 4-pyridyl and $R_2$ is a para substituted phenyl.

Advantageous compounds of this invention are the compounds of Formula A in which $R_1$ is 4-pyridyl and $R_2$ is 4-fluorophenyl or its sulfoxide, said compounds being 5-(4-pyridyl)-6-(4-fluorophenyl)-2,3-dihydroimidazo[2,1-b]thiazole and its 1-oxide derivative as well as their acid addition salts.

Of course it is understood that $R_1$ and/or $R_2$ may be unsubstituted phenyl while the substituted phenyl containing compounds for A, V or VI are preferred.

Other advantageous compounds of this invention are compounds of Formula A in which $R_2$ is 4-ethoxy-phenyl, 4-chlorophenyl or 4-methylthio. Also, compounds of Formula A in the form of the sulfoxide are preferred.

The compounds of this invention are prepared by the following procedure:

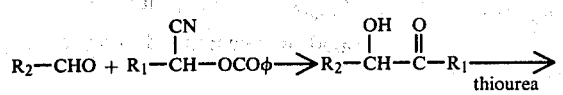

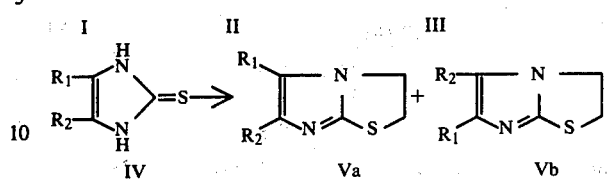

The required substituted 2-mercaptoimidazoles (IV) are prepared by condensing a phenyl-pyridyl-α-hydroxy ketone or a pyridoin (III) with thiourea in a high boiling polar solvent such as dimethylformamide, dimethylacetamide, dimethylsulfoxide, or hexanol using conditions similar to those of the procedure described by P. M. Kochergin, Zhur. Obshchei Khim., 31:1093 (1961), Chem. Abstr., 55:23503f. We believe the 2-mercapto intermediates are new compounds and these with their S-alkyl derivatives are part of our invention.

In the final step of the overall reaction sequence (I→V), compounds of this invention are prepared by alkylation of a 4,5-diaryl-2-mercaptoimidazole (IV) with an ethylene 1,2-dihalide such as 1-bromo-2-chloroethane in dimethylformamide, dimethylsulfoxide, dimethyl acetamide or other polar solvents. The alkali metal salt of the mercapto intermediate is formed by treatment with a sodium or potassium hydride prior to addition of the dihalide. The reaction is then allowed to proceed at about room temperature for convenience overnight.

The products of the reaction are a mixture of the two isomers in which the imidazolyl substituents ($R_1$ and $R_2$) are transposed. After the reaction at room temperature a solid alkali metal carbonate is added followed by a reflux period. The reaction mixture is then quenched in ice-water to give the isomeric mixture. Other methods of isolation known to the art may be optionally used.

The individual isomers are separated by fractional crystallization or chromatography.

The sulfoxide compounds, that is the compounds of Formula A, for example, in which the 1-sulfinyl group is present, are prepared by oxidation of the 2,3-dihydroimidazo[2,1-b]thiazoles (V), preferably with one equivalent of m-chloroperbenzoic acid in a solvent such as methylene chloride or with a similar sulfur oxidizing agent such as sodium or potassium periodate, hydrogen peroxide or other organic peracids.

The sulfone compounds, that is the compounds of Formula A, for example in which the 1-sulfonyl group is present, are obtained by oxidation of the corresponding 2,3-dihydroimidazo[2,1-b]thiazoles (V) or their sulfoxide derivative with two or one equivalents of oxidizing agent, respectively, in a suitable organic solvent. If an oxidizable thio substituent is present on the phenyl ring it may also be oxidized by similar methods.

One skilled in the art will recognize that the N-oxide derivative of the pyridyl substituents can also be prepared using somewhat stronger oxidizing conditions. These are also a part of this invention.

As stated above the 2-mercapto-imidazole intermediates (V) which may alternatively be named as the tautomeric 2-thiones are new compounds and are part of this invention. The 2-mercaptans may also be converted into their lower alkyl or polyhaloloweralkyl thioether derivatives of the oxides thereof.

This group of compounds is exemplified by the structural formula:

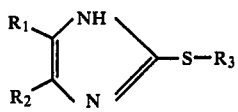

in which $R_1$ and $R_2$ are as defined above and $R_3$ is hydrogen or a lower alkyl of 1-6 carbon atoms such as isopropyl, butyl, isobutyl, amyl, ethyl, methyl or a stable polyhaloalkyl of 1-6 carbon atoms especially polyfluoroalkyl groups such as tetrafluoroethyl, trifluoromethyl, perfluoroethyl, trifluoroethyl and others.

Generally speaking the mercaptans, VI in which $R_3$ is hydrogen have their chief utility as intermediates. The thioether derivatives are especially of use in having potent antiarthritic activity in the tests outlined hereafter. Expecially active are those compounds of Formula VI in which $R_2$ is a 4-substituted phenyl with substituents such as fluoro, methoxy or methylthio and $R_3$ is isopropyl or tetrafluoroethyl. The mono-, di- or polyoxides of the compounds of VI are also part of this invention.

N-Phenyl-4,5-dipyridyl-2-mercaptoimidazoles has been reported in the literature F. Friedrich et al., Pharmazie 24:429 (1969) [C.A. 71:101772] or also see U.S. Pat. No. 3,252,799. A number of monoaryl substituted-2-mercaptoimidazoles are known, for example, German Pat. No. 2,338,279 or Japanese Pat. No. 2,083,372. See also U.S. Pat. No. 3,707,475 for pyridylsubstituted imidazoles which lack the thio substituent at the 2-position which structural feature distinguishes the diarylimidazoles of this invention (VI).

The 2-mercapto intermediates are generally prepared by reacting the pyridylhydroxy ketone (III) with thiourea usually in dimethyl formamide, dimethylacetamide or the like at reflux temperature. The intermediates may be optionally isolated using conventional chemical techniques.

The pharmaceutically acceptable acid addition salts of the compounds of Formulas A, V or VI are formed with strong or moderately strong organic or inorganic acids by methods known to the art. It will be appreciated that there is one basic center in the imidazole ring and another for each pyridyl.

For example, the base is reacted with an organic or inorganic acid in aqueous miscible solvent, such as ethanol or isopropanol, with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The N or S oxide derivatives of A, V or VI are also part of this invention and are prepared as described above and in the Examples.

The compounds of this invention (A, V and VI) have utility as chemical intermediates, intermediates for the preparation of dyestuffs or as pharmacodynamic agents. In the latter area activity has been demonstrated in standard pharmacological test procedures for determining antiarthritic, antiinflammatory or immunoregulatory properties. In general, but especially in the 2,3-dihydro[2,1-b]thiazole series, the sulfoxide derivatives often are more active than their parent compounds. Also the mixed 5-pyridyl-6-phenyl compounds are more active than are their dipyridyl or 6-phenyl-5-pyridyl congeners.

Activity useful in the treatment of arthritis may be determined by the following test procedures:

Inhibition of adjuvant induced polyarthritis in rats, as measured by reduction of raw paw edema, is produced by compounds of this invention at daily doses of about 12.5-100 mg/kg orally. In this test procedure, adjuvant arthritis in rats is produced by a single intradermal injection of 0.75 mg of *Mycobacterium butyricum* suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to protect the animals against the development of both primary and secondary lesions of adjuvant arthritis.

Species of this invention which demonstrate weak to moderate activity in this test are 6-(4-methoxyphenyl)-5-(4-pyridyl)-2,3-dihydroimidazo[2,1-b]thiazole, its sulfoxide and 6-(4-methylthiophenyl)-5-(4-pyridyl)2,3-dihydroimidazo[2,1-b]thiazole. The 2-mercaptoimidazoles of Formula VI which have demonstrated activity in this test are: 2-(2-propylthio)-4-(4-methoxyphenyl)-5-(4-pyridyl)imidazole, its sulfoxide and sulfone; 2-(propylthio)-4-(4-methylthiophenyl)-5-(4-pyridyl)-imidazole and its bissulfone; 2-(1,1,2,2-tetrafluoroethylthio)-4-(4-methoxyphenyl)-5-(4-pyridyl)imidazole; 2-(2-propylthio)-4-(4-fluorophenyl)-5-(4-pyridyl)imidazole; 2-(1,1,2,2-tetrafluoroethylthio)-4-(4-methylthiophenyl)-5-(4-pyridyl)-imidazole; 2-(1,1,2,2-tetrafluoroethylsulfonyl)-4-(4-methoxyphenyl)-5-(4-pyridine-N-oxide)imidazole.

In the carrageenan induced raw paw edema test, antiinflammatory activity is produced by the active compounds of this invention at doses of about 25–100 mg/kg orally.

In addition, compounds which have immunoregulatory activity provide benefit for treatment of rheumatoid arthritis. Stiller et al., *Annals of Internal Medicine* 82:405–410 (1975), Froland et al., *Scandinavian J. Immunol.* 3:223–228 (1974) and *The Lancet*, Jan. 11, 1975, page 111. It has been found that species of this invention demonstrate the ability to regulate cell-mediated immunity as shown in procedures such as the oxazolone-induced contact sensitivity test procedure in which mouse paw is measured. This procedure is described by Griswold et al., *Cellular Immunology* 11:198–204 (1974).

Species of this invention which demonstrate good activity in the oxazolone test are 6-(4-fluorophenyl)-5-(4-pyridyl)-2,3-dihydroimidazo[2,1-b]thiazole, its sulfoxide, 5,6-di(2-pyridyl)-2,3-dihydroimidazo[2,1-b]-thiazole-1-oxide and 6-(4-methoxyphenyl)-5-(4-pyridyl)-2,3-dihydroimidazo[2,1-b]-thiazole. The 2- mercapto imidazoles of Formula VI which have demonstrated activity in this test are: 2-(1,1,2,2-tetrafluoroethyl)-4-(4-methoxyphenyl)-5-(4-pyridyl)imidazole; 2-(2-propylthio)-4-(4-fluorophenyl)-5-(4-pyridyl)imidazole; 2-(2-propylsulfonyl)-4-(4-methanesulfonylphenyl)-5-(4-pyridyl)imidazole; 2-(2-propylsulfonyl)-4-(4-methoxyphenyl)-5-(4-pyridyl)imidazole; 2-(1,1,2,2-tetrafluoroethylthio)-4-methylthiophenyl)-5-(4-pyridyl)imidazole.

In addition to having utility in rheumatoid arthritis, immunoregulatory agents have potential utility in other diseases where cell mediated immunity is compromised. Examples of such diseases are systemic lupus erythematosus and autoimmune thyroiditis (Stiller et al. cited hereabove). Also, diseases such as atopic dermatitis, recurrent aphthus ulceration, recurrent upper respiratory tract infections in children and flu, lung and breast cancer, transient granulocylopenia and allergic skin reactions have been successfully treated with levamisole which is an agent which restores impaired cell mediated immune response [Symoens et al., *Journal of the Reticuloendothelial Society*, 21:175-221 (1977)].

The pharmaceutically effective compounds of this invention are administered in conventional dosage forms prepared by combining a compound of Formula I in an amount sufficient to produce antiarthritic or other activity with standard pharmaceutical carriers according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

To obtain a stable water soluble dose form, a pharmaceutically acceptable acid addition salt, preferably sulfate, of a compound of Formula A the base is dissolved in an aqueous solution of an organic or inorganic acid, such as a 0.3 M solution of succinic acid or, preferably, citric acid. In addition to sulfate, exemplary of other water soluble salts are methanesulfonate, phosphate and hydrochloride.

Preferably, each dosage unit will contain the active ingredient in an amount of from about 50 mg. to about 200 mg.

The method of producing antiarthritic activity by administering internally to an animal a pharmaceutically effective quantity of a compound of Formula I is also an object of this invention. The compound of Formula I is administered in an amount sufficient to produce antiarthritic activity. The route of administration may be orally or parenterally. The daily dosage regimen will be preferably from about 100 mg. to about 1 g.

When the method is carried out as described above, antiarthritic activity is produced.

One skilled in the art will recognize that in determining the amounts of the active ingredient in the claimed compositions and used in the claimed methods, the relative activity of the chemical ingredient in the test procedures outlined compared with a standard compound such as levamisole as well as the size of the host animal must be considered.

The term "lower alkyl" and lower alkoxy" where used herein denote groups having preferably 1-5 carbon atoms especially methyl, ethyl, methoxy or ethoxy, respectively.

The following examples are not limiting but are illustrative of the invention. Temperatures are on the Centigrade scale.

EXAMPLE 1

Preparation of the 2-Thione Starting Material

To an aqueous solution (75 ml) of sodium cyanide (19.6 g; 400 mm) and benzyltriethyl ammonium chloride (3.0 g, 13 mm) was added isonicotinaldehyde (10 g, 93 mm) in 100 ml of methylene chloride at 0° temperature. Vigorous stirring was maintained for 15 minutes and a methylene chloride solution of benzoyl chloride (14.0 g, 100 mm, 50 ml) was slowly added. Cooling was discontinued after one-half hour reaction and the mixture was allowed to reach ambient temperature. The organic layer was separated and washed with 5% sodium carbonate and brine, dried and evaporated to an oil which was thoroughly extracted with ether (4 l). The ethereal solution was concentrated to approximately 500 ml and allowed to crystallize to give 5.0 g of isonicotinaldehyde-o-benzoylcyanohydrin. The cyanohydrin (3.0 g, 12 mm) was stirred in 50 ml of tert.-butyl alcohol with the substituted benzaldehyde (12 mm) and sodium hydride (12 mm) was added. Stirring continued for 1½ hours at room temperature and a mineral oil suspension of potassium hydride (24% suspension, 4 ml, 23 mm) was added with caution. A thin layer chromatographic assay of an aliquot of the reaction mixture after 1½ hours indicated the formation of a single product. This was worked up by quenching the suspension in 200 ml of ice-water mixture and extracting with chloroform. The chloroform extract was evaporated to a crystalline residue which was further crystallized by the addition of ether. A crystalline product was obtained which could be further purified by crystallization from methylene chloride-ether mixtures.

2-(4-methylthiophenyl)-2-hydroxy-1-(4-pyridyl)-ethanone; (60%) m.p. 127°-130°.

Anal. Calcd. ¼ H$_2$O: C, 63.73; H, 5.15; N, 5.31; Found: C, 63.33; H, 5.12,; N, 5.31.

2-(4-methoxyphenyl)-2-hydroxy-1-(4-pyridyl)ethanone; (50%).

Anal. Calcd. 1 H$_2$O: C, 68.55; H, 6.16; N, 5.70; Found: C, 68.29; H, 5.31; N, 5.65.

The above procedure was used with p-fluorobenzaldehyde but the intermediate was not isolated but was used directly in the next step.

9.0 G. (37 mm) of the hydroxy ketone was refluxed in 140 ml of dimethylformamide with 5.3 g (70 mm) of thiourea. Starting material was no longer detected after 4 hours of reaction and the solvent was concentrated to one half of the original volume to initiate the precipitation of the crystalline 2-mercaptoimidazole; crystallization was completed overnight in the refrigerator. The compounds were purified by trituration or crystallization from ethanol.

4-(4-Methoxyphenyl)-5-(4-pyridyl)-2-mercaptoimidazole was formed in 68% yield; m.p. 280°.

4-(4-Methylthiophenyl)-5-(4-pyridyl)-2-mercaptoimidazole was formed in 65% yield; m.p. 350°.

Anal. Calcd.: C, 60.17; H, 4.38; N, 14.03; Found: C, 60.11; H, 4.71; N, 14.25.

4-(4-Fluorophenyl)-5-(4-pyridyl)-2-mercaptoimidazole was formed in 40% overall yield of crude material based on the benzoyl cyanohydrin condensation, m.p. 386°–388°.

Anal. Calcd. ¼ H₂O: C, 61.46; H, 3.78; N, 15.39; Found: C, 61.58; H, 4.21; N, 15.11.

EXAMPLE 2

Formation of the Isomeric 5/6-Pyridyl-6/5-Phenyl-2,3-Dihydroimidazo[2,1-b]Thiazoles The mercaptoimidazole (12.5 mm) was suspended in 100 ml of dimethylformamide and sodium hydride (13.0 mm) was added. Salt formation was allowed to proceed at room temperature for ½ hour at which time 1-bromo-2-chloroethane was added from a syringe and the solution was stirred overnight under an argon atmosphere.

Solid anhydrous potassium carbonate (20.0 mm) was added to the reaction mixture and reflux was initiated for 2½ hours. Dilution of the dimethylformamide solution with ice-water mixture to 300 ml, caused precipitation of the organic products which were purified as described below.

EXAMPLE 3

Purification and Separation of 6-(4-Methoxyphenyl)-5-(4-Pyridyl)-2,3-Dihydroimidazo[2,1-b]Thiazole (Va) and 5-(4-Methoxyphenyl)-6-(4-Pyridyl)-2,3-Dihydroimidazo[2,1-b]Thiazole (Vb)

The oily organic residue from the procedure of Example 2 was triturated with isopropanol and crystallized. The crystalline material that separated out was almost pure Va, ($R_f$ 0.2 silica/ether). This preferred 6-(4-methoxyphenyl)-5-(4-pyridyl)isomer was recrystallized from chloroform-ether, m.p. 170°–172°; 1.5 g.

Anal. Calcd.: C, 66.00; H, 4.89; N, 13.58; Found: C, 65.74; H, 4.98; N, 13.86.

The mother liquor of the crystallization deposited a second crop of crystalline material, mainly Vb ($R_f$ 0.3, silica/ether). The mother liquor of this 2nd crop was then chromatographed on silica using the dry column technique with ethyl acetate. The faster moving substance was eluted, combined with the second crop of the isopropanol crystallization and both crystallized from chloroform-ether yielding 0.7 g, m.p. 187°–188°, of the 5-(4-methoxyphenyl)-6-(4-pyridyl)isomer.

Anal. Calcd. ¼ H₂O: C, 65.05; H, 4.98; N, 13.39; Found: C, 65.34; H, 4.89; N, 13.58.

EXAMPLE 4

Purification and Separation of 6-(4-Methylthiophenyl)-5-(4-Pyridyl)-2,3-Dihydroimidazo[2,1-b]Thiazole and 5-(4-Methylthiophenyl)-6-(4-Pyridyl)-2,3-Dihydroimidazo[2,1-b]Thiazole The oily residue from the procedure of Example 2 was extracted into ether (2×150 ml) and chloroform (2×100 ml). The ethereal extract deposited 1.5 g of a crystalline material, the chloroform extract was evaporated and taken up in isopropanol, ether was added (40 ml) to establish a 1:1 ratio and allowed to crystallize. The yield of this second fraction was 1.00 g. Both crystalline fractions were mixtures of the two 5,6-isomers which were separated by chromatography using silica with 20% isopropanol-ether solvent. The faster moving spot ($R_f$ 0.60, silica/ether-isopropanol) was first eluted and was further purified by crystallization from ether-chloroform, m.p. 210°–213°, 0.6 g of the 5-(4-methylthiophenyl-6-(4-pyridyl)isomer.

Anal. Calcd. ¼ H₂O: C, 61.88; H, 4.73; N, 12.73; Found: C, 62.16; H, 4.93; N, 12.57.

The slower moving spot consisted mainly of the desired 6-(4-methylthiophenyl)-5-(4-pyridyl)isomer ($R_f$ 0.22) and was recrystallized from chloroform-ether (1:1), m.p. 190°–193°, yield: 0.4 g.

Anal. Calcd. ¼ H₂O: C, 61.88; H, 4.73; N, 12.73; Found: C, 61.99; H, 4.87; N, 12.54.

EXAMPLE 5

Purification and Separation of 6-(4-Fluorophenyl)-5-(4-Pyridyl)-2,3-Dihydroimidazo[2,1-b]Thiazole and 5-(4-Fluorophenyl)-6-(4-pyridyl)-2,3-Dihydroimidazo[2,1-b]-Thiazole The oily residue from the procedure of Example 2 was chromatographed on silica using the dry column technique with 1:1 ethyl acetate/ether. This separated the isomeric mixture from all impurities. The isomers were then separated by medium pressure liquid chromatography on silica with isopropanol/ether (1:2). The faster moving spot ($R_f$ 0.55, silica/isopropanol) after elution was further purified by crystallization from isopropanol, m.p. 165°–167°, yield 0.75 g of the 5-(4-fluorophenyl)-6-(4-pyridyl)isomer.

Anal. Calcd.: C, 64.63; H, 4.07; N, 14.13; Found: C, 64.85; H, 4.12; N, 14.12.

The slow moving spot, the preferred 5-(4-pyridyl)-6-(4-fluorophenyl)isomer ($R_f$ 0.25, silica/isopropanol) after elution was recrystallized from isopropanol: m.p. 186°–189°, 0.62 g.

Anal. Calcd.: C, 64.63; H, 4.07; N, 14.13; Found: C, 64.27; H, 4.10; N, 14.05.

This compound is converted to its pharmaceutically acceptable acid addition salts such as the dihydrochloride, sulfate, methanesulfonate and others by reaction of the base with an excess of acid in an organic solvent such as isopropanol.

EXAMPLE 6

6-(4-Methoxyphenyl)-5-(4-Pyridyl)-2,3-dihydroimidazo[2,1-b]Thiazole-1-Oxide

To 2.4 g of 6-(4-methoxyphenyl)-5-(4-pyridyl)-2,3-dihydroimidazo[2,1-b]thiazole in 200 ml methylene chloride was added 1.34 g of m-chloroperbenzoic acid in 150 ml of methylene chloride at ice-bath temperature. After 10 minutes the reaction mixture was diluted with methylene chloride and washed twice with 100 ml of 5 N sodium carbonate. Evaporation of the dried extracts left a solid which when recrystallized from chloroform-ether gave 1.6 g of the title product, m.p. 165°–170°.

Anal. Calcd.: C, 61.06; H, 4.82; N, 1257; Found: C, 60.71; H, 4.41; N, 12.47.

EXAMPLE 7

6-(4-Fluorophenyl)-5-(4-Pyridyl)-2,3-Dihydroimidazo-[2,1-b]Thiazole-1-Oxide

To 1.9 g of 6-(4-fluorophenyl)-5-(4-pyridyl)-2,3-dihydroimidazo[2,1-b]thiazole in 25 ml of methylene chloride cooled to ice-bath temperature was added 1.36 g of m-chloroperbenzoic acid. Stirring was continued for 1 hour then the solution was diluted with methylene chloride and washed with a 1:1 mixture of 5% sodium carbonate and brine. Treating with magnesium sulfate, filtering and stripping gave 2.1 g of the title product which was triturated with ether, filtered and dried to give 1.8 g, m.p.229°-231°.

Anal. Calcd.: C, 61.33; H, 3.86; N, 13.41; Found: C, 61.61; H, 4.18; N, 13.46.

Treating the starting material with 2.72 g of m-chloroperbenzoic acid gives the 1-dioxide derivative.

EXAMPLE 8

4-(4-Fluorophenyl)-5-(4-Pyridyl)-2-(2-Propylthio)Imidazole

To 8.0 g of 4-(4-fluorophenyl)-5-(4-pyridyl)-1H-imidazole-2-thione in 100 ml of dimethylformamide was added 1.56 g of sodium hydride (50% in mineral oil). The mixture was stirred until the evolution of hydrogen ceased. At this point 3.9 g of isopropyl bromide was added with a syringe. After stirring for 3 hours the mixture was poured into water, filtered and air dried. Trituration with ether, filtering and drying gave 5.73 g. Recrystallizing a 3.0 g sample from ethanol gave 1.4 g of the title compound, m.p. 263°-264°.

Anal. Calcd.: C, 65.15; H, 5.15; N, 13.41; Found: C, 65.36; H, 4.99; N, 13.19.

EXAMPLE 9

2-(2-Propylthio)-4-(4-Methoxyphenyl)-5-(4-Pyridyl)Imidazole 4-(4-Methoxyphenyl)-5-(4-pyridyl)-2-mercaptoimidazole (2.2 g, 8 mm) was covered with 25 ml of dimethylformamide and sodium hydride (13 mm) was added. 2-Bromopropane (1.10 g, 9.5 mm) was added in a dimethylformamide solution (20 ml) and the reaction was allowed to stir at room temperature overnight. Pouring the solution into water precipitated the product which was taken up in chloroform, dried and evaporated to an oil which crystallized by the addition of ether. Yield of the title product was 1.5 g, m.p. 206°-210°.

Anal. Calcd.: C, 66.52; H, 5.89; N, 12.93; Found: C, 66.46; H, 6.10; N, 13.00.

EXAMPLE 10

2-(2-Propylsulfinyl)-4-(4-Methoxyphenyl)-5-(4-Pyridyl)-Imidazole

The 2-isopropylthioimidazole from Example 9 (11.1 g, 35 mmole) was suspended in 300 ml of methylene chloride and placed in an ice-bath. m-Chloroperbenzoic acid (7.5 g) was added in 100 ml. of methylene chloride over the period of 40 minutes. The solution was stirred for an additional 15 minutes and organic solution extracted with sodium bicarbonate (5%). The aqueous alkaline extract was discarded and the organic layer was dried and evaporated to give a semi-solid which was recrystallized from methylene chloride-ether yielding 7.5 g of a crystalline solid which was further purified by chromatography (alumina). The pure product was obtained from chloroform elution: 180°-181.5°.

Anal. Calcd.: C, 63.32; H, 4.61; N, 12.31; Found: C, 63,37; H, 5.64; N, 12.34.

EXAMPLE 11

2-(2-Propylthio)-4-(4-Methylthiophenyl)-5-(4-Pyridyl)-Imidazole

The 2-mercaptoimidazole precursor (8.0 g, 27 mm) was dissolved in 100 ml of dimethylformamide and sodium hydride (1.35 g, 28 mm, 50% oil) was added under argon. The 2-bromopropane (37 g, 30 mmoles) was transferred into this solution at room temperature with a syringe and the mixture was allowed to stir for 3½ hours. The reaction was quenched by dilution with water to 600 ml and the solid precipitate was filtered. Crystallized from chloroform-ether (1:1) to yield 6.5 g of crystalline material. The analytical sample melted at 219°-222°.

Anal. Calcd.: C, 63.31; H, 5.61; N, 12.30; Found: C, 63,58; H, 5.87; N, 12.03.

EXAMPLE 12

2-(1,1,2,2-Tetrafluoroethylthio)-4-(4-Methoxyphenyl)-5-(4-Pyridyl)Imidazole

The 2-mercaptoimidazole precursor (4.0 g, 14 mm) was suspended in 100 ml of dimethylformamide and purged with argon in a pressure flask, sodium hydride (200 mg, 50% oil) was added and the pressure flask was filled with tetrafluoroethylene gas to 28 psi. A pressure drop was almost immediately noticeable and the pressure was maintained at 28-30 psi by allowing more gas to enter intermittently. The reaction was thought to be complete after 2½ hours when complete dissolution of the starting material was observed. The reaction mixture was poured into water, neutralized with dilute hydrochloric acid to pH 6 and and the precipitate filtered. Recrystallization from chloroform-ether gave 3.2 g of the title product, m.p. 212°-214°.

Anal. Calcd.: C, 53.26; H, 3.42; N, 10.96; Found: C, 52.95; H, 3.57; N, 10.78.

EXAMPLE 13

2-(1,1,2,2-Tetrafluoroethylthio)-4-(4-Methylthiophenyl)-5-(4-Pyridyl)Imidazole A stirred suspension of 3.5 g of the 2-mercaptoimidazole (11.7 mm) in 100 l. of dimethylformamide and was purged with argon in a glass pressure flask. Sodium hydride (100 mg) was added and the apparatus was pressurized with tetrafluoroethylene gas to 28-30 psi. The pressure was maintained for 5 hours at room temperature, periodically recharging the flask. The solution was filtered and the filtrate was diluted with water (500 ml). The cloudy suspension was extracted with methylene chloride and the organic extract was dried and evaporated to an oil. This crude material was placed on a silica column and eluted with ether-cyclohexane (2:1). The first few fractions yielded the desired title product. Recrystallized from chloroform-cyclohexane. Yield, 1.8 g, m.p. 204°-205°.

Anal. Calcd.: C, 51.12; H, 3.28; N, 10.52; Found: C, 51.41; H, 3.50; N, 10.84.

EXAMPLE 14

5,6-Di-(2-Pyridyl)-2,3-Dihydroimidazo[2,1-b]Thiazole

A solution of 2.14 g (0.02 m) of α-pyridoin and 1.52 g (0.02 m) of thiourea in 50 ml of dimethylformamide was refluxed 2.5 hours. The cooled solution was poured into 100 ml of water and the product was allowed to crystallize from the mixture. The mixture was filtered and the crude product was washed thoroughly with water, and air dried to yield 1.7 g of brown solid. The crude product was recrystallized from 80 ml methanol (charcoal) to yield 1.0 g off-white crystals, m.p. 280°–285°. A sample of the 2-thione was recrystallized from 60 ml methanol, m.p. 282°–283°.

Anal. Calcd. ½ $H_2O$: C, 59,30; H, 4.21; N, 21.28; Found: C, 59.48; H, 4.15; N, 21.33.

A mixture of 16.57 g (0.065 m) of 4,5-di(2-pyridyl)-1H-imidazole-2-thione in 150 ml of dimethylformamide was stirred at −15° (ice-methanol-dry ice) under nitrogen and 27 ml (6.2 g, 0.15 m) of a 24% suspension of potassium hydride in mineral oil was added gradually. After about 2 hours, a solution of 11.8 g (5.42 ml, 0.0634 m) of dibromoethane in 60 ml of dimethylformamide was added dropwise. The reaction mixture was allowed to attain room temperature overnight. The mixture was poured into 600 ml of water. The aqueous mixture was extracted with 3×200 ml portions of methylenechloride. The combined extracts were washed with 5×100 ml water, brine, dried over magnesium sulfate, and evaporated in vacuo. The residue was triturated under 25 ml of low boiling petroleum ether. The product was separated, dissolved in 50 ml of ethanol. The solution was chilled until crystallization was complete, filtered, and the product was washed with a small portion of cold ethanol and air dried. Yield 9.1 g, m.p. 140°–142°. Crystallization three times from ethanol gave an analytical sample of 5,6-di-(2-pyridyl)-2,3-dihydroimidazo[2,1-b]thiazole, m.p. 142°–143°.

The base (500 mg) is dissolved in a minimal quantity of isopropanol. Ethanolic hydrogen chloride is added in excess. The mixture is evaporated and washed with ether to give the trihydrochloride salt. Other acid addition salts as outlined above are similarly prepared.

Running this reaction with β-pyridoin or γ-pyridoin gives 5,6-di-(3-pyridyl)-2,3-dihydroimidazo[2,1-b]thiazole or 5,6-di-(4-pyridyl)-2,3-dihydroimidazo[2,1-b]thiazole, respectively.

EXAMPLE 15

5,6-Di-(2-Pyridyl)-2,3-Dihydroimidazo[2,1-b]Thiazole-2-Oxide

A 4.26 g (0.02 m) portion of sodium periodate was added to a solution of 5.26 g (0.0189 m) of 5,6-di-(2-pyridyl)-2,3-dihydroimidazo[2,1-b]thiazole in 200 ml of methanol and 5 ml of dioxane. The mixture was stirred over the weekend at room temperature. The mixture was filtered and stripped. The residue was taken up in 100 ml of hot chloroform, filtered, and the filtrate was stripped. The residue was recrystallized four times from methanol to yield 3.5 g white crystals, m.p. 195°–197°. An analytical sample was prepared by recrystallization from methanol, m.p. 199°–200°.

Anal Calcd.: C, 60.80; H, 4.08; N, 18.91; Found: C, 60.73; H, 3.92; N, 19.12.

EXAMPLE 16

2-Propylsulfonyl)-4-(4-Methanesulfonylphenyl)-5-(4-Pyridyl)-Imidazole

The 2-(2-propylthio)-4-(4-methylthio)-5-(4-pyridyl)-imidazole of Example 11 (3.0 g, 9 mm) was dissolved in 100 ml of methylene chloride and the solution was cooled to 0°–5° in an ice-bath. m-Chloroperbenzoic acid (5.5 g, 27 mm) was added in a single portion and the reaction was allowed to come to ambient temperature within an hour. The resultant suspension was extracted with 5% sodium bicarbonate solution. The washed organic layer was dried and evaporated to a glassy bisdioxide residue which was crystallized from chloroform-ethanol-ether (1:1.2); m.p. 248°–250°.

Anal. Calcd.: C, 53.31; H, 4.72; N, 10.36; Found: C, 53.22; H, 4.80; N, 10.02.

EXAMPLE 17

2-(2-Propylsulfonyl)-4-(4-Methoxyphenyl)-5-(4-Pyridyl)-Imidazole 2-(2-Propylthio)-4-(4-methoxyphenyl)-5-(4-pyridyl)-imidazole (9.1 g, 28 mm) was suspended in 250 ml of methylenechloride, cooled to 0°–5° in an ice-bath and m-chloroperbenzoic acid (12.3 g, 60 mm) was added in 100 ml of methylene chloride over the period of one-half hour. The organic solution was washed with 5% sodium carbonate, dried and evaporated to a dioxide solid. The crystalline solid was recrystallized from chloroform-ethyl ether-methanol (2:2:½) mixture, m.p. 262°–266°.

Anal. Calcd. ½ $H_2O$: C, 59.0; H, 5.50; N, 11.46; Found: C, 59.23; H, 5.46; N, 11.32.

EXAMPLE 18

4-(4-Methoxyphenyl)-5-(4-N-Oxypyridyl)-2-(1,1,2,2-Tetrafluoroethylsulfonyl)Imidazole The 4-(4-methoxyphenyl)-5-(4-pyridyl)-2-(1,1,2,2-tetrafluoroethylthio)imidazole (2.3 g, 6.0 mm) was dissolved in 40 ml of acetic acid and heated to 70°–75° in a water-bath. 30% Hydrogen peroxide (2.5 ml) was added and heating was maintained for 1½ hours. A thin layer assay of the reaction mixture indicated the presence of partially oxidized products and the reaction was extended for an additional hour with 33 ml additional quantities of the peroxide.

The acetic acid solvent was evaporated at reduced pressure, and the residual oil was diluted with water to obtain a solid which was crystallized from chloroform-ethanol (1:1) mixture; m.p. 252°–253°.

Anal. Calcd.: C, 47.53; H, 3.03; N, 9.74; Found: C, 47.89; H, 2.95; N, 9.62.

EXAMPLE 19

2-(1,1,2,2-Tetrafluoroethylthio)-4-(4-Fluorophenyl)-5-(4-Pyridyl)Imidazole

To a 250 ml high pressure bottle was added 5 g of 4-(4-pyridyl)-5-(4-fluorophenyl)-1H-imidazole-2-thione and 100 ml of dimethylformamide. Argon was bubbled through the suspension for 10 min., then 0.2 g sodium hydride (50% in mineral oil) was added. The bottle was then flushed 5 times with tetrafluoroethylene then pressurized to 55 psi for 3 hours. The suspension completely dissolved after 1½ hours of stirring at room temperature. After an additional 1 hour of stirring the material was poured into water filtered and dried. Four recrystallizations from aqueous dimethylformamide gave 1.2 g of the title compound: m.p. 242°-248°.

Anal. Calcd.: C, 51.75; H, 2.71; N, 11.32; Found: C, 51.49; H, 2.87; N, 11.07.

EXAMPLE 20

Using the methods outlined above especially those of Examples 1, 2 and 3 but using the following benzaldehydes:

p-trifluoromethylbenzaldehyde
o-bromobenzaldehyde
m-chlorobenzaldehyde
p-methylbenzaldehyde
p-ethylbenzaldehyde
m-isopropoxybenzaldehyde gives:

5-(4-pyridyl)-6-(4-trifluoromethylphenyl)-2,3-dihydroimidazo[2,1-b]thiazole
6-(2-bromophenyl)-5-(4-pyridyl)-2,3-dihydroimidazo-[2,1-b]thiazole
6-(3-chlorophenyl)-5-(4-pyridyl)-2,3-dihydroimidazo[2,1-b]thiazole
6-(4-methylphenyl)-5-(4-pyridyl)-2,3-dihydroimidazo[2,1-b]thiazole
6-(4-ethylphenyl)-5-(4-pyridyl)-2,3-dihydroimidazo-[2,1-b]thiazole, and
6-(3-isopropoxyphenyl)-5-(4-pyridyl)-2,3-dihydroimidazo-[2,1-b]thiazole, together with their respective 2-thione intermediates and 5/6 isomers.

EXAMPLE 21

| Ingredients | Amounts |
|---|---|
| 5-(4-Pyridyl)-6-(4-fluorophenyl)-2,3-dihydroimidazo[2,1-b]thiazole | 100 mg. |
| Magnesium stearate | 5 mg. |
| Lactose | 50 mg. |

The above ingredients are screened, mixed and filled into a hard gelatin capsule. The capsule is administered to a patient in need of treatment for arthritis in quantities of from 1-6 times daily orally.

EXAMPLE 22

| Ingredients | Amounts |
|---|---|
| 2-(2-Propylthio)-4-(4-methoxyphenyl)-5-(4-pyridyl)-imidazole | 150 mg. |
| Calcium Sulfate Dihydrate | 100 mg. |
| Sucrose | 20 mg. |
| Starch | 5 mg. |
| Talc | 5 mg. |
| Stearic Acid | 3 mg. |

The sucrose, calcium sulfate dihydrate and the imidazole are mixed and granulated with 10% gelatin solution. The wet granules are screened, dried, mixed with the starch, talc and stearic acid, screened and compressed into a scored tablet. The tablet is administered to an arthritic patient orally in quantities from 1-6 times daily.

In similar fashion other active species of this invention may be converted into dosage units and administered using active quantities based on their activities in the given tests compared with the species of Examples 21 and 22 and the standard drug, levamisole.

What is claimed is:

1. A compound of the structure:

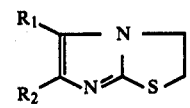

in which:

$R_1$ and $R_2$, being the same or different but at least one being pyridyl, are pyridyl or phenyl optionally monosubstituted by a lower alkoxy, lower alkyl, lower alkylthio, chloro, fluoro, bromo, or trifluoromethyl, or a pharmaceutically acceptable acid addition salt or oxide derivative thereof.

2. A compound of claim 1 in which $R_1$ is 4-pyridyl and $R_2$ is a phenyl monosubstituted by lower alkoxy, lower alkyl, lower alkylthio, chloro, fluoro or bromo or trifluoromethyl, its 1-sulfoxide derivative or a pharmaceutically acceptable acid addition salt thereof.

3. A compound of claim 1 in which $R_1$ is 4-pyridyl and $R_2$ is 4-methoxyphenyl or a pharmaceutically acceptable acid addition salt thereof.

4. A compound of claim 1 in which $R_1$ is 4-pyridyl and $R_2$ is 4-fluorophenyl or a pharmaceutically acceptable acid addition salt thereof.

5. A compound of claim 1 in which $R_1$ is 4-pyridyl and $R_2$ is 4-fluorophenyl as a pharmaceutically acceptable oxide derivative thereof.

6. A compound of claim 1 in which $R_1$ is 4-pyridyl and $R_2$ is p-methoxyphenyl, p-ethoxyphenyl or p-fluorophenyl, or a pharmaceutically acceptable salt or oxide derivative thereof.

7. A compound of claim 5 which is the form of the free base.

8. A compound of claim 5 which is the form of a dihydrochloride salt.

9. A compound of claim 1 in which $R_1$ and $R_2$ are both pyridyl in the form of its 1-sulfoxide.

10. A compound of claim 1 in which $R_1$ and $R_2$ are both 2-pyridyl.

11. The method of inducing antiarthritic activity in an animal or human subject in need thereof comprising administering orally or parenterally to said subject an effective nontoxic quantity of a compound of claims 1 or 6.

12. A pharmaceutical composition having antiarthritic activity comprising a dosage unit adapted for oral or parenteral administration containing an effective, nontoxic quantity of an active ingredient of claims 1 or 6.

13. The composition of claim 12 in which the quantity of an active ingredient is selected from the dose range of from about 50-200 mg.

* * * * *